(12) United States Patent
Frank et al.

(10) Patent No.: US 7,458,966 B2
(45) Date of Patent: Dec. 2, 2008

(54) MEDICAL INSTRUMENT

(75) Inventors: Timothy Graham Frank, Fife (GB); Alfred Cuschieri, Fife (GB); Duncan Martin, Dundee (GB); James Gove, Dundee (GB)

(73) Assignee: University of Dundee (GB)

( * ) Notice: Subject to any disclaimer, the term of this patent is extended or adjusted under 35 U.S.C. 154(b) by 472 days.

(21) Appl. No.: 10/848,800

(22) Filed: May 19, 2004

(65) Prior Publication Data

US 2005/0033355 A1    Feb. 10, 2005

Related U.S. Application Data

(63) Continuation of application No. PCT/EP03/05083, filed on May 15, 2003.

(30) Foreign Application Priority Data

Jun. 1, 2002    (DE) ............................. 102 24 336

(51) Int. Cl.
*A61B 17/00* (2006.01)
(52) U.S. Cl. ..................... 606/1; 606/174; 606/206; 606/207
(58) Field of Classification Search ............... 606/74, 606/113, 72, 151, 61, 103, 1
See application file for complete search history.

(56) References Cited

U.S. PATENT DOCUMENTS

| 1,600,381 A | 9/1926 | Wright |
| 4,569,131 A | 2/1986 | Falk et al. ............... 30/251 |
| 4,950,273 A | 8/1990 | Briggs ..................... 606/113 |
| 5,458,579 A | 10/1995 | Chodorow et al. ........... 604/165 |
| 6,053,921 A | 4/2000 | Wagner et al. ................ 606/74 |
| 6,436,122 B1 * | 8/2002 | Frank et al. ................. 606/208 |

FOREIGN PATENT DOCUMENTS

| DE | 75 20 824.1 | 1/1976 |
| DE | 41 15 548 A1 | 11/1991 |
| DE | 43 34 746 A1 | 4/1995 |
| DE | 44 13 520 A1 | 10/1995 |
| DE | 199 12 038 C1 | 1/2001 |
| DE | 199 18 483 C1 | 1/2001 |
| EP | 0 157 888 | 10/1985 |
| SU | 1319837 | 6/1987 |

* cited by examiner

*Primary Examiner*—Lee S Cohen
(74) *Attorney, Agent, or Firm*—St. Onge Steward Johnston & Reens LLC

(57) ABSTRACT

The invention relates to a medical instrument, in particular an endoscopic instrument, with an instrument shaft, a tool positioned on the distal end of the instrument shaft, and a handle, which can be secured on the instrument shaft so that it can be moved in an axial extension of the instrument shaft. In order to create an instrument which makes possible a comfortable, safe, and reliable handling even with the most varied application purposes, it is proposed with the invention that the handle can be secured on the instrument shaft so that it can be moved by at least one degree of freedom with respect to the instrument shaft.

20 Claims, 2 Drawing Sheets

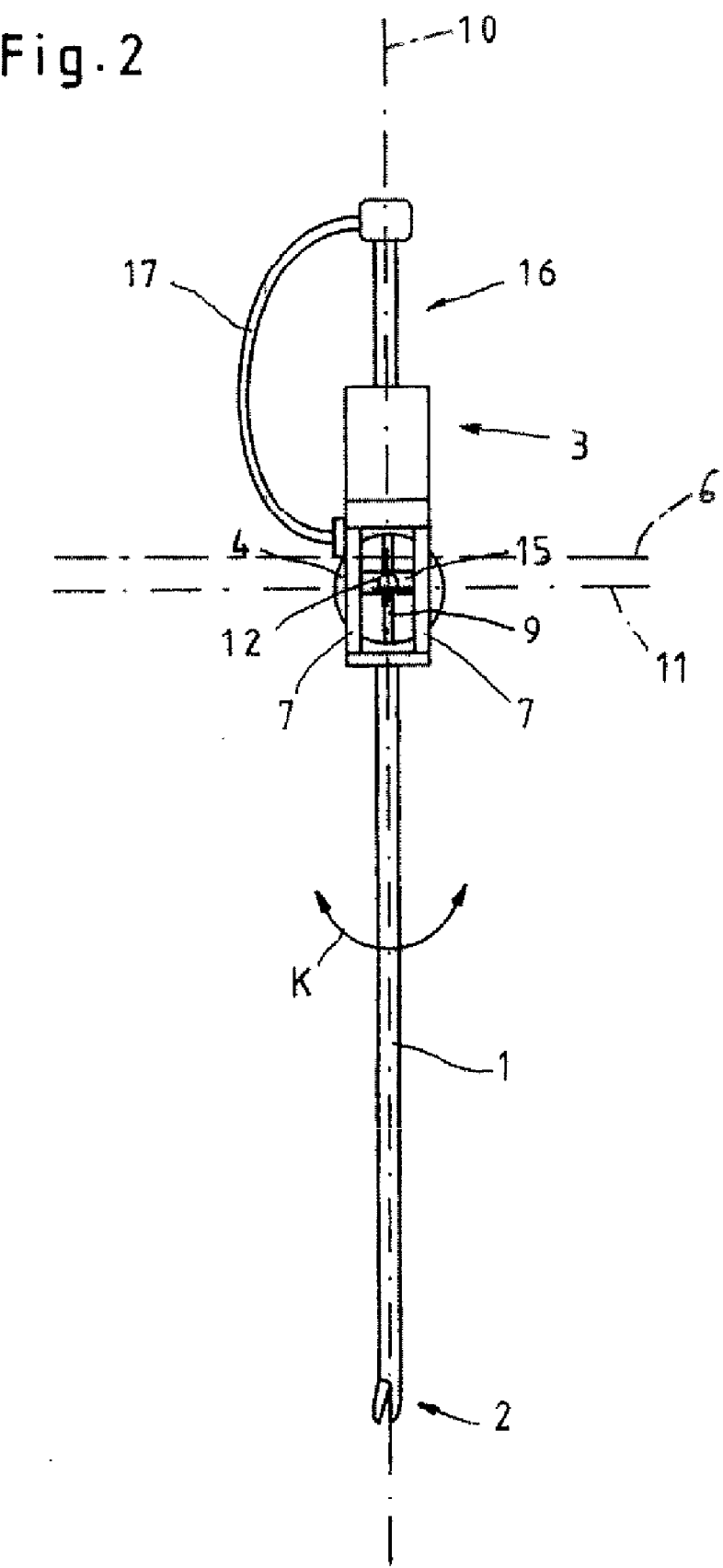

MEDICAL INSTRUMENT

This application is a continuation of pending International Patent Application No. PCT/EP03/05083 filed May 15, 2003 which designates the United States and claims priority of pending German Application No. 10224336.0 filed Jun. 1, 2002.

FIELD OF INVENTION

The invention relates to a medical instrument, in particular an endoscopic instrument, with an instrument shaft, a tool positioned on the distal end of the instrument shaft, and a handle that can be secured on the instrument shaft so that it can be moved by means of a coupling element as an axial extension of the instrument shaft.

With instruments for laparoscopic surgery in particular, medical instruments frequently have shaft lengths of 30 cm and more. This shaft length ensures that even operating areas located at some distance can be reached, without the need to change the instrument's location. However, because the instruments spend the most time in closer operating areas, most of the length of the instrument shaft is found outside the patient's body. This can result in an unfavorable and uncomfortable posture or working position for the surgeon, because the handle for guiding and/or activating the surgical instrument is located at the proximal end of the instrument shaft.

This problem becomes still more serious in HALS (Hand Assisted Laparoscopic Surgery) technique, in which, in addition to inserting the laparoscope and sometimes laparoscopic instruments into the peritoneal cavity, an incision is sometimes made to allow insertion of the surgeon's hand so that the surgeon can conduct a more effective operation using tactile sense while observing and monitoring through the laparoscope. While the surgeon supports the operation by keeping one hand in the patient's peritoneal cavity, with the other hand he or she activates the laparoscopic instruments. A handle arranged far out at the end of the instrument shaft makes the surgeon's work considerably more difficult.

From German Patent DE 44 13 520 A1, a device is known for placing trocars or puncturing nozzles. This device consists essentially of a handle having two gripping parts and of a transport mechanism, arranged in the handle housing, by means of which the instrument shaft of a trocars or of a puncturing nozzle inserted into the handle housing can be moved in the direction of the puncture spot.

The actual transport mechanism, by means of which the instrument shaft can be transportable through the handle housing, in this known device, according to a first embodiment, consists of a spring-loaded clamping mechanism and, according to a second embodiment, of a toothed gear between a gripping portion of the handle and the instrument shaft.

This known device has the disadvantage that the handle, in the design with the tooth-geared transport mechanism, can be secured on the instrument shaft exclusively in the longitudinal direction of the instrument shaft. In the configuration of the transport mechanism with the spring-loaded clamping mechanism, there is the at least theoretical possibility of also turning the handle around the longitudinal axis of the instrument shaft, so that in this case, where the instrument shaft is concerned, at most two degrees of freedom are available for handling the device.

To ensure that the surgeon has a safe, comfortable handling of a medical instrument at all times, an adjustable handling, as here described, is not sufficient.

In addition, from DE 199 12 038 C1 a medical instrument is known whose handle can swivel with respect to the instrument shaft in order to allow the surgeon an always sufficient angle for grasping the handle. This swivel handle facilitates the surgeon's work in unfavorable space conditions to a very considerable degree, but unfavorable working positions, which result primarily from the length of the instrument shaft, cannot be remedied, or at least not sufficiently, by this swivel capacity.

Consequently, it is the object of the invention to create a medical instrument of the aforementioned type, which, even with the most varied application purposes, allows for comfortable, safe, and reliable handling.

The invention fulfills this objective in that the handle can be secured to the instrument shaft so that it is adjustable with respect to the instrument shaft by at least three degrees of freedom.

Thanks to the invention design, for the operator of the handle that can be removably secured along the longitudinal length of the shaft, it is now possible to mount the handle on the instrument shaft and individually adjust it so that an optimal position of the handle is available for each operating phase and so that the medical instrument can be managed comfortably and safely.

According to a practical embodiment of the invention, the coupling element is configured as the component that at least partially surrounds the instrument shaft and can be clamped together with the instrument shaft. The clamping of the coupling element with the instrument shaft ensures that the handle can be secured immovably on the instrument shaft and that a movement exerted on the handle can be transmitted to the instrument shaft.

In a preferred embodiment of the invention it is proposed that the distal end of the handle is configured as a tensioning device to receive the coupling element, so that a pressure force can be exerted by means of the tensioning device in such a way that the coupling element surrounds the instrument shaft, at least partially clamping the shaft.

To create a coupling element which ensures a safe grip at and on the instrument shaft and, in addition, is simple and cost-effective to produce, it is proposed with the invention that the coupling element is configured as an essentially cylindrical or spherical component with a penetration bore hole for the instrument shaft and that the tensioning device of the handle is configured as a bearing for rotatable storage of the coupling element.

In this configuration the coupling element and the tensioning device form a type of ball joint which makes possible additional swiveling and tipping of the handle in relation to the instrument shaft. Thus, together with the longitudinal extension of the handle along the instrument shaft and the rotation of the instrument shaft, this embodiment of the invention results in four degrees of freedom for the handle mounted on the instrument shaft, namely a translation motion in the direction of the longitudinal axis of the instrument shaft and three rotation movements, one around the longitudinal axis of the instrument shaft and two around an axis perpendicular to the longitudinal axis of the instrument shaft.

In this alternative configuration of the invention, it is proposed that the coupling element, configured as a spherical-shaped component, has, at least on one side, an aperture running from the outer perimeter to the penetration bore hole and configured in the axial direction of the instrument shaft.

It is further proposed with the invention that the spherical-shaped coupling element consists of at least two spherical elements divided in the axial direction of the instrument shaft. The configuration of the coupling element, for instance from two half-spheres, allows for simple, rapid mounting of the coupling element on the instrument shaft and allows tensing of the coupling element even when hard materials are used.

According to a first embodiment of the invention, the coupling element consists of a compressible material, especially a rubber or plastic material.

A second embodiment of the invention also allows the use of non-compressible materials, such as hard synthetics or hard metallic material, to form the coupling element, since the at least one aperture allows a clamping of the coupling element with the instrument shaft by the exertion of an external pressure.

To create a handle that is easily produced and safe to use, it is proposed with the invention that the handle has two handgrips on the proximal side, so that at least one handgrip is swivel-mounted for movement around a swivel axis relative to the other handgrip.

To avoid forcing the surgeon to permanently hold together the handgrips of the handle in order to keep the handle securely joined to the instrument shaft, the handle can be locked in a closed position in which the coupling element is clamped together with the instrument shaft, and in order to lock the handle in the closed position a locking device is mounted on the handle, which lock device is preferably configured as a threaded screw-in joint or eccentric lock mounted in the area of the tensioning device.

It is further proposed with the invention that the screw-in mounting of the coupling element in the tensioning device can be restricted by stop pin so that the handle can be locked tightly in position on the instrument shaft in a precise posture with respect to the instrument shaft.

In an additional practical embodiment of the invention it is proposed that, in a medical instrument with a tool mounted on the distal end of the instrument shaft, the tool is activated by means of the handgrips of the handle, so that the handle and the tool are connected to one another by means of at least one power transmission device. The power transmission device in this case is preferably configured as a flexible power transmission element, in particular a Bowden cable or hydraulically driven power transmission device.

In a preferred embodiment of the invention, in addition to activation of the tool by means of the handgrips of the handle, the tensioning device can also be activated by the handgrips of the handle. In this embodiment it is advantageous if the activation of the tensioning device by the handgrips of the handle can be uncoupled from the activation of the tool by the handgrips of the handle.

It is particularly effective to uncouple the activation function of the handgrips if at the same time as the selection of an activation function, the other activation function is automatically shut off, and for this purpose a turn-off device for locking the activation function that can be exerted by the handgrips of the handle is mounted on the handle.

Additional objects and advantages of the invention will be set forth in the description of the related illustration which follows, in which an embodiment of a medical instrument according to the invention is presented by way of example.

BRIEF DESCRIPTION OF THE DRAWINGS

FIG. 2 shows a rear view of the medical instrument depicted in FIG. 1.

DETAILED DESCRIPTION OF EMBODIMENTS

Figure 1:
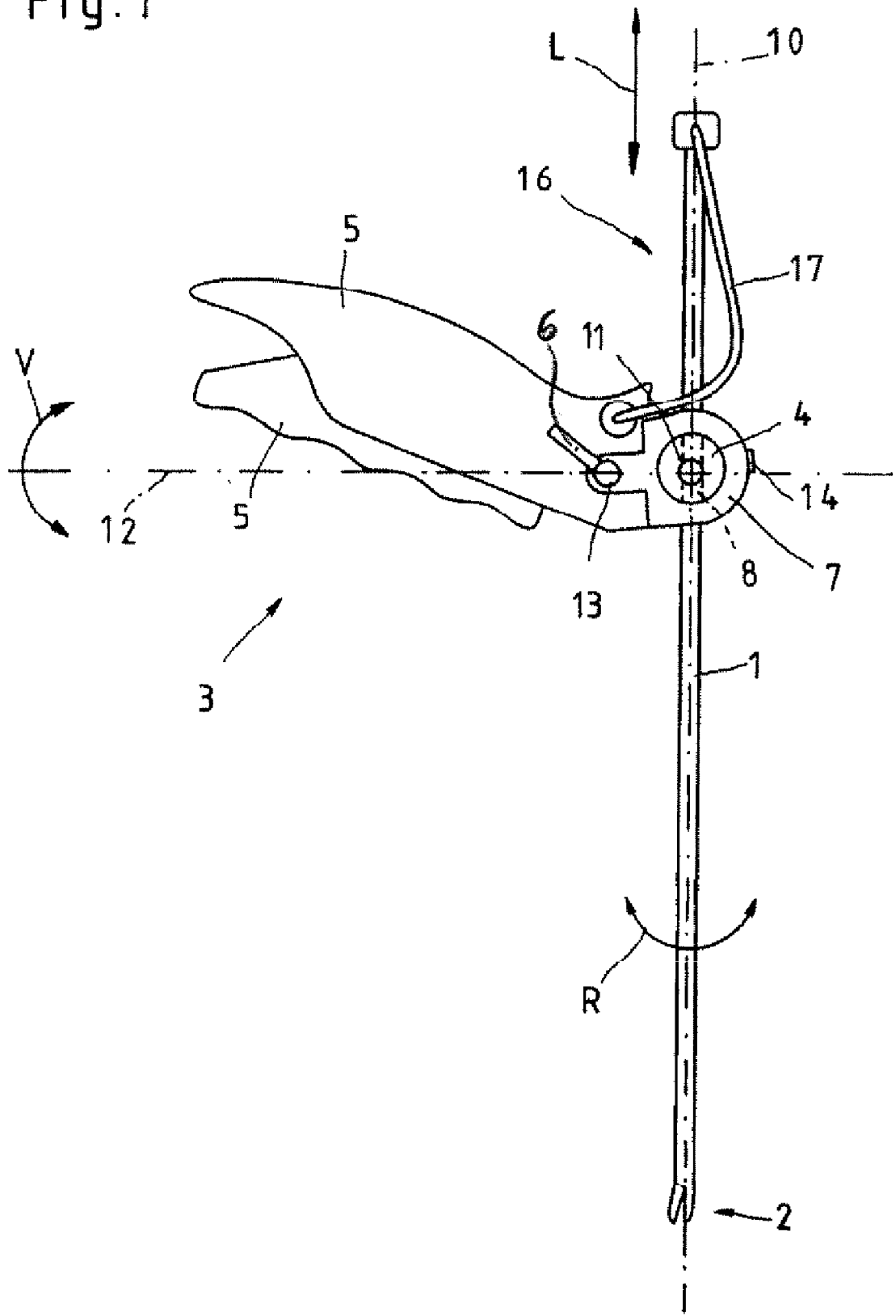
FIG. 1 shows a side view of a first embodiment of a medical instrument according to the invention.

The medical instrument illustrated in FIGS. 1 and 2 consists essentially of a lengthy cylindrical instrument shaft 1, a tool 2 configured as a grasping tool mounted on the distal end of the instrument shaft 1, and a handle 3 for manipulating the instrument shaft 1 and/or the grasping tool 2.

It is noteworthy in the illustrated medical instrument that the handle 3, contrary to known medical instruments that are customary in the state of the art, is not mounted immovably on the proximal end of the instrument shaft 1 but instead can be secured by clamping in an axial extension of the instrument shaft 1 at any desired spot on the instrument shaft 1.

The handle 3 is secured by clamping to the instrument shaft 1 by means of a coupling element 4, which is configured as a component that at least partially surrounds the instrument shaft 1. In this embodiment illustrated here, the coupling element 4 is a ball-shaped component. It is also possible, of course, to configure the coupling element 4 as, for instance, a cylindrical component that at least partially surrounds the instrument shaft 1.

As can further be seen from the illustrations, the handle 3, which can be adjustably secured on the instrument shaft 1, in the illustrated embodiment of a medical instrument has two handgrips 5 on the proximal side, at least one of which can swivel around a swivel axis 6 in relation to the other handgrip 5. The distal end of the handle 3 forms a tensioning device 7, which serves to receive the coupling element 4.

The ball-shaped coupling element 4, which has a penetration hole 8 bored for the instrument shaft 1, consists according to FIGS. 1 and 2 of two semi-spherical ball segments divided in the axial direction of the instrument shaft 1 and which are rotatably mounted in the tensioning device 7 of the handle 3 that is configured as a bearing.

The tensioning device 7 can exert a pressurized force on the coupling element 4 which causes the coupling element 4 to clamp on and surround the instrument shaft 1. If the coupling element 4 consists of a compressible material, such as a rubber or plastic material, the malleability of the material is sufficient to produce a pressure-locked connection between the handle 3 and the instrument shaft 1 by means of the pressurized force, and this connection ensures that the handle 3 is securely locked in an exact position on the instrument shaft 1.

If, on the other hand, the coupling element 4 consists of a non-compressible or inelastic, non-malleable material, such as a hard synthetic or a metal material, then the coupling element 4 has at least one aperture 9 running from the outer perimeter to the penetration bore hole 8, in the axial direction of the instrument shaft 1. When the tensioning device 7 exerts the pressurized force, this aperture 9 is closed and thus the coupling element 4 is clamped in a pressure-locked connection with the instrument shaft 1.

In this configuration of the coupling element 4 as composed of two semi-spherical ball elements, the coupling element 4 thus has two apertures 9 at a 180 degree angle to one another.

On the basis of the described configuration of the handle 3, which can be secured by means of the coupling element 4 on the instrument shaft 1, the surgeon has the freedom to select the position of the handle 3 at will. If the operating area is close to the point of entry into the patient's body, the surgeon can position the handle 3 far from the distal end of the instrument shaft 1 in order to avoid an unfavorable working posture. If the instrument shaft, on the other hand, is required for an operating area farther removed from the point of entry, the handle 3 can be quickly and easily moved to the proximal end.

In addition to the possibility of moving the handle 3, by translated force in the direction of the longitudinal axis 10 of the instrument shaft 1, the handle 3 can be rotated around the longitudinal axis 10 of the instrument shaft 1 so that, in this basic construction of the handle 3 that can be secured on the instrument shaft 1, the handle 3 has at least two degrees of freedom with respect to the longitudinal axis 10 of the instrument shaft 1, namely one for a translating motion and one for a rotating motion.

In the embodiment illustrated in FIGS. 1 and 2, in which the coupling element 4 is a spherical component, forming a type of ball-joint, rotatably mounted in the bearing of the tensioning device 7, there are two additional rotating degrees of freedom for the motion of the handle 3 with respect to the instrument shaft 1. These two additional degrees of freedom are, first, the swivel capacity of the handle 3 around the axle 11, which is perpendicular to the longitudinal axis 10 of the instrument shaft 1, according to FIG. 1, and second, the tippable mounting of the handle 3 around the axle 12, which is perpendicular to the longitudinal axis 10 of the instrument shaft 1, according to FIG. 2.

A handle 3 of this type is distinguished, therefore, in having four degrees of freedom, by which it can be moved with respect to the instrument shaft 1, so that the handle 3 can be switched easily and quickly into any position desired by the surgeon in order to ensure comfortable, safe, and reliable handling of the medical instrument.

To guarantee that the handle 3 remains secured and exactly placed in the position that has been selected on the instrument shaft 1, the handle 3 can be locked in the clamped closed position on the instrument shaft 1 by means of a stopping device 13. In addition, the rotatable storage of the coupling element 4 in the tensioning device 7 can be restricted by means of a lock pin 14 positioned in the area of the tensioning device 7. As soon as it has thus been ensured, by means of the stopping device 13, that the coupling element 4 is clamped together with the instrument shaft 1, the surgeon can direct the medical instrument safely and comfortably with the handle 3, since the adjustability of the tensioning device 7 is now blocked.

In the embodiment illustrated in FIGS. 1 and 2, the stopping device 13 consists of a screw thread 15 by means of which, as can be seen in FIG. 2, both side walls of the tensioning device 7 are drawn inward toward one another so that the spherical segments of the coupling element 4 are pressed in a clamping motion against the instrument shaft 1.

As an alternative to the use of a screw thread 15 as a stopping device 13, other appropriate means are also possible of course, such as the configuration of an eccentric lock, in order to exert a durable pressurized force on the coupling element 4 by means of the tensioning device 7, so that the handle is held locked in an exact location on the instrument shaft 1.

In the medical instrument illustrated in FIGS. 1 and 2, a tool 2 is positioned on the distal end of the instrument shaft 1. To operate this grasping tool 2 by means of the handle 3, the handle 3 is connected with the grasping tool 2 by means of a power transmission element 16, which preferably is guided by the hollow instrument shaft 1. The grasping tool 2 is activated by means of the handgrips 5 of the handle 3. In this medical instrument illustrated in FIGS. 1 and 2, the power transmission element 16 is a Bowden cable 17. When the power transmission element 16 takes the form of a Bowden cable 17, to open the tool 2 on the distal side requires the presence of a readjusting spring, which is not shown in the illustration.

Other power transmission elements 14 are also possible of course, such as for instance the use of a hydraulically driven power transmission element.

A handle 3 as previously described, which can be secured at any point on an instrument shaft 1, can also be used, of course, for other medical instruments in which a tool is activated, not simultaneously, by means of the handle 3 in or on the instrument shaft 1. In these configurations, therefore, no power transmission element is connected with the handle 3.

A medical instrument of the design shown in FIGS. 1 and 2 is operated as follows:

In the working position illustrated in FIG. 1, the handle 3 is clamped to the instrument shaft 1 tightly and at an exact location in such a way that the surgeon can comfortably and safely operate the medical instrument and especially the tool 2 positioned at the distal end of the instrument shaft 1 by means of handgrips 5 of the handle 3.

Now, if for instance, if work is to be performed at an operating area further removed from the point of entry of the instrument into the patient's body, the surgeon can displace the handle 3 farther to the proximal end of the instrument shaft 1. For this purpose, the surgeon activates the stopping device 13 as well as the lock pin 14, so that the handle 3, taking advantage of the available four degrees of freedom, can now be displaced with respect to the instrument shaft 1. As soon as the handle 3 has reached the optimal position for the surgeon, the stopping device 13 as well as the lock pin 14 are again activated in order to secure the handle 3 tightly and at an exact location on the instrument shaft 1 again.

FIG. 1 shows three degrees of freedom of the adjustability of the handle 3 with respect to the instrument shaft 1, namely the translation movement in the direction of the longitudinal axis 10 of the instrument shaft 1 with the arrow L, the rotation around the longitudinal axis 10 of the instrument shaft 1 with the arrow R, and the rotatability around the axis 11 that runs perpendicular to the longitudinal axis 10 of the instrument shaft 1 with arrow V.

The possible fourth degree of freedom is shown in FIG. 2, indicating with arrow K the rotatable tippable mobility of the handle 3 around the axis 12 running perpendicular to the longitudinal axis 10 of the instrument shaft 1.

KEY TO REFERENCE NUMBERS

1 Instrument shaft
2 (Grasping) Tool
3 Handle
4 Coupling element
5 Handgrip
6 Swivel axis
7 Tensioning device
8 Penetration bore hole
9 Aperture
10 Longitudinal axis
11 Axis
12 Axis
13 Stopping device
14 Lock pin
15 Screw thread
16 Power transmission element
17 Bowden cable
L Arrow (longitudinal mobility)
K Arrow (tippability)
R Arrow (rotation)
V Arrow (swivel capacity)

What is claimed is:

1. An endoscopic medical instrument, comprising:
   an instrument shaft;
   a tool positioned on a distal end of the instrument shaft;
   a handle; and
   a coupling element securing the handle on the instrument shaft so that the handle can be moved by at least three degrees of freedom with respect to the instrument shaft, wherein one of the degrees of freedom is a translation movement in the direction of a longitudinal axis of the instrument shaft.

2. A medical instrument as in claim 1, wherein the coupling element is configured as a component that at least partially surrounds the instrument shaft and can be clamped together with the instrument shaft.

3. A medical instrument as in claim 1, wherein a distal end of the handle is configured as a tensioning device to receive the coupling element.

4. A medical instrument as in claim 3, wherein a pressure force can be exerted on the coupling element by the tensioning device in such a way that the coupling element at least partially surrounds the instrument shaft while clamping said instrument shaft.

5. A medical instrument as in claim 4, wherein the coupling element is configured as an essentially spherical component equipped with a penetration bore hole for the instrument shaft and the tensioning device of the handle is configured as a bearing for rotatable storage of the coupling element.

6. A medical instrument as in claim 5, wherein the coupling element configured as a spherical component has, at least on one side, an aperture running from an outer perimeter of the coupling element to the penetration bore hole and configured in the axial direction of the instrument shaft.

7. A medical instrument as in claim 5, wherein the spherical coupling element consists of at least two spherical segments divided in the axial direction of the instrument shaft.

8. A medical instrument as in claim 7, wherein the coupling element consists of a compressible material including a rubber or plastic material.

9. A medical instrument as in claim 7, wherein the coupling element consists of a non-compressible material including a hard synthetic or metallic material.

10. A medical instrument as claim 9, wherein the handle has two handgrips wherein at least one handgrip is positioned so that it can pivot around a swivel axis with respect to the other handgrip.

11. A medical instrument as in claim 10, wherein the handle can be stopped in a closed position, in which the coupling element is clamped together with the instrument shaft.

12. A medical instrument as in claim 11, wherein a stopping device is positioned on the handle to stop the handle in the closed position.

13. A medical instrument as in claim 12, wherein the stopping device is configured as a screw thread in the area of the tensioning device.

14. A medical instrument as in claim 12, wherein the stopping device is an eccentric stopping device mounted in the area of the tensioning device.

15. A medical instrument as in claim 5, wherein rotation of the coupling element can be restricted in the tensioning device by means of a lock pin.

16. A medical instrument as in claim 15, wherein the tool can be activated by a handgrip of the handle and the handle and the tool are connected to one another by at least one power transmission device.

17. A medical instrument as in claim 16, wherein the at least one power transmission device is configured as a flexible power transmission element.

18. A medical instrument as in claim 17, wherein the at least one power transmission device is configured as a Bowden cable.

19. A medical instrument as in claim 16, wherein the at least one power transmission device is hydraulically powered.

20. An endoscopic medical instrument, comprising:
   an instrument shaft;
   a tool positioned on a distal end of the instrument shaft;
   a handle;
   a coupling element securing the handle on the instrument shaft so that the handle can be moved by at least three degrees of freedom with respect to the instrument shaft;
   wherein a distal end of the handle is configured as a tensioning device to receive the coupling element;
   wherein a pressure force can be exerted on the coupling element by the tensioning device in such a way that the coupling element at least partially surrounds the instrument shaft while clamping said instrument shaft; and
   wherein the coupling element is configured as an essentially spherical component equipped with a penetration bore hole for the instrument shaft and the tensioning device of the handle is configured as a bearing for rotatable storage of the coupling element.

* * * * *